United States Patent [19]

Benjamin

[11] 4,064,760
[45] Dec. 27, 1977

[54] STERILE URINE COLLECTION DEVICE

[75] Inventor: Thomas A. Benjamin, Glen Gardner, N.J.

[73] Assignee: IPCO Hospital Supply Corporation, White Plains, N.Y.

[21] Appl. No.: 750,591

[22] Filed: Dec. 15, 1976

[51] Int. Cl.² ............................................. G01N 1/20
[52] U.S. Cl. .................................... 73/421 R; 4/110; 128/2 F
[58] Field of Search ............. 73/421 R; 128/2 F, 295, 128/272, 294; 4/110; 232/43; 141/331; 215/6, 232, 228

[56] References Cited

U.S. PATENT DOCUMENTS

| | | | |
|---|---|---|---|
| 2,278,754 | 4/1942 | Wolcott | 141/331 |
| 2,791,148 | 5/1957 | Maisch | 141/331 |
| 3,777,739 | 12/1973 | Raitto | 128/2 F |
| 3,830,107 | 8/1974 | Linzer | 73/421 R |
| 3,878,571 | 4/1975 | Seeley | 128/2 F |
| 3,881,465 | 5/1975 | Raitto | 128/2 F |

*Primary Examiner*—Charles A. Ruehl
*Assistant Examiner*—Denis E. Corr

[57] ABSTRACT

A mid-stream urine collection device whereby the specimen container is kept completely uncontaminated before, during and after use. The collection device includes a container and a container closing lid having an opening therein. A funnel assembly is mounted over the lid having a funnel member which extends through the opening in the lid. A funnel cover is mounted over the funnel assembly and a seal is provided on the device and which is adapted to be removed from the device and to be applied to the lid and over the opening therein to close the opening in the lid after the container is used.

21 Claims, 11 Drawing Figures

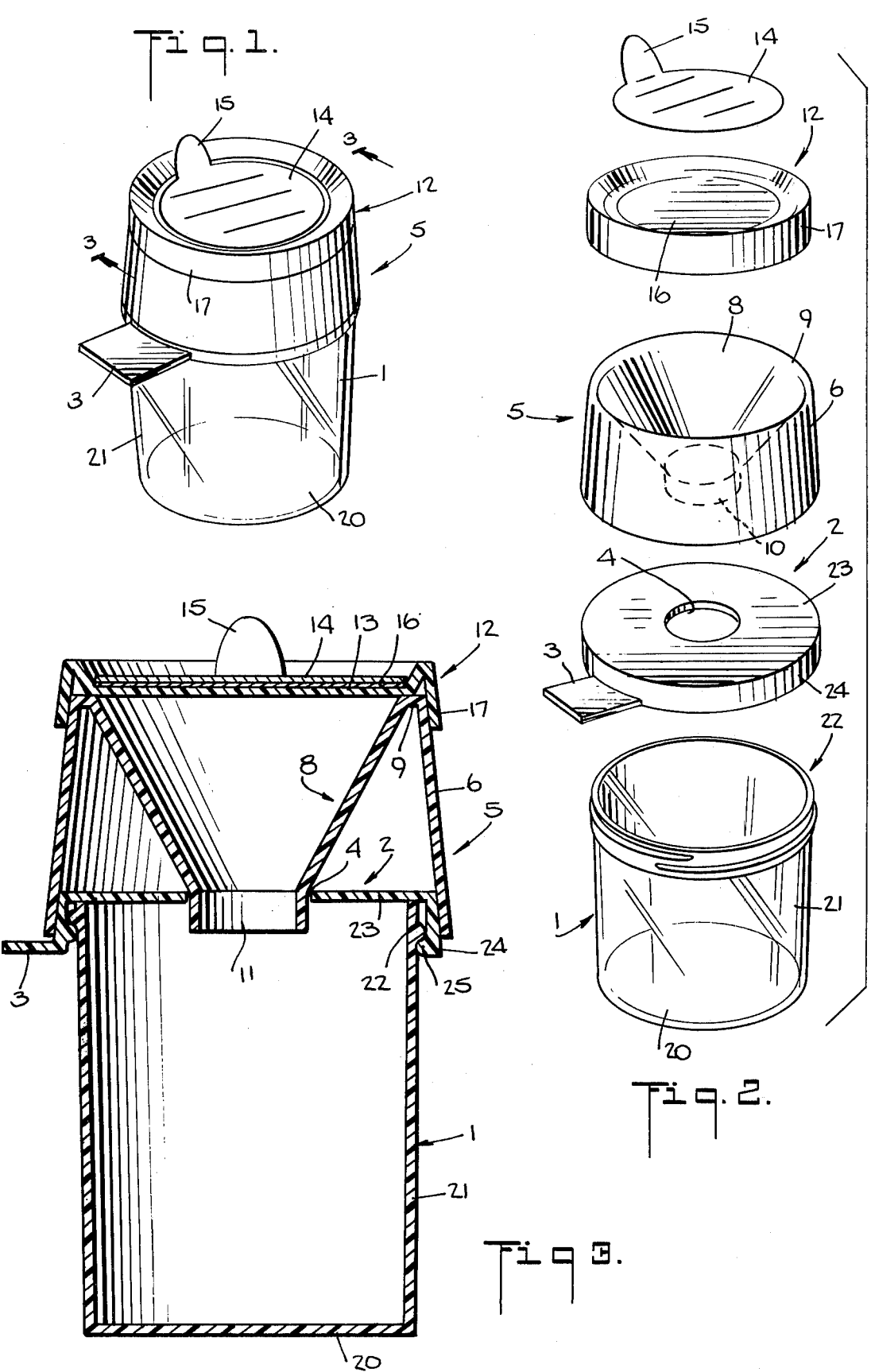

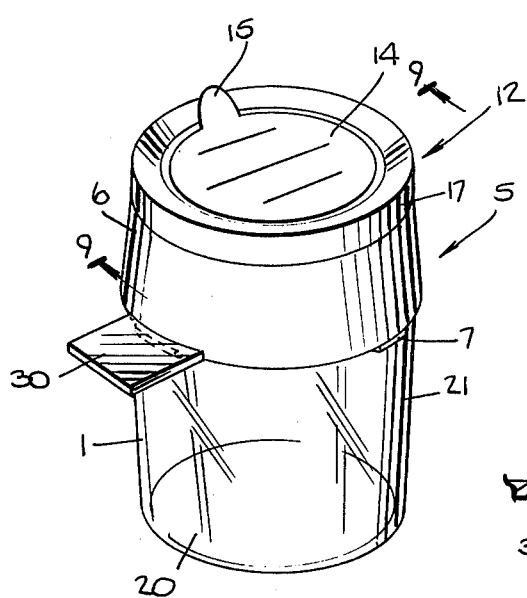
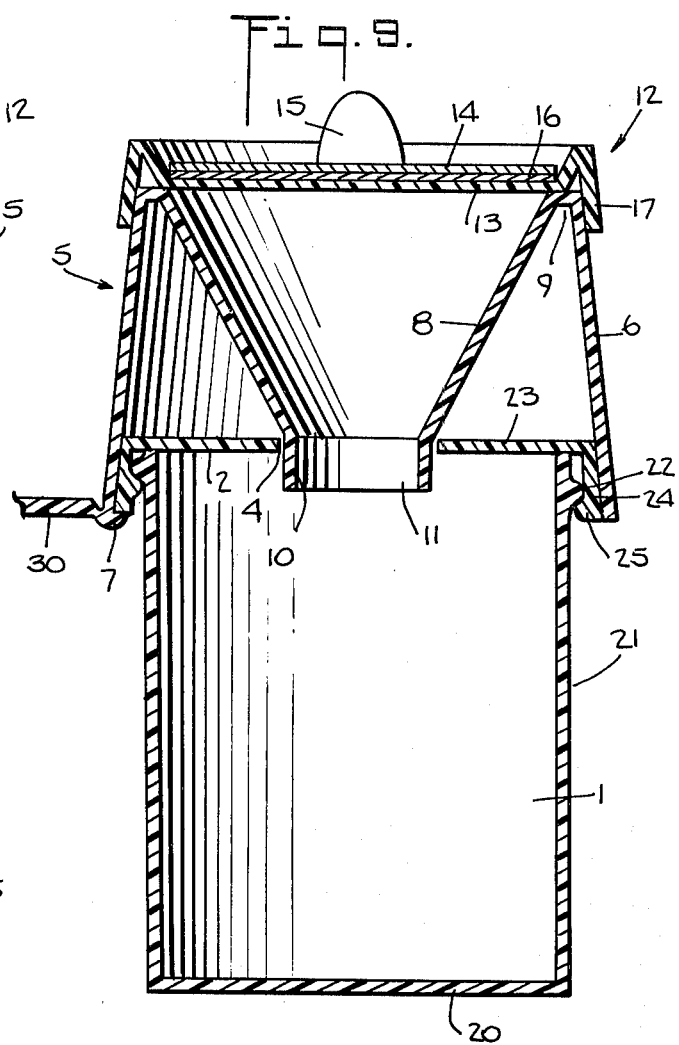
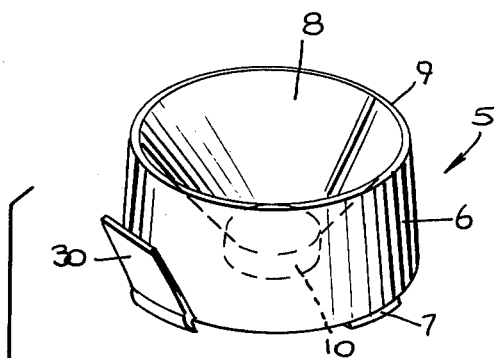
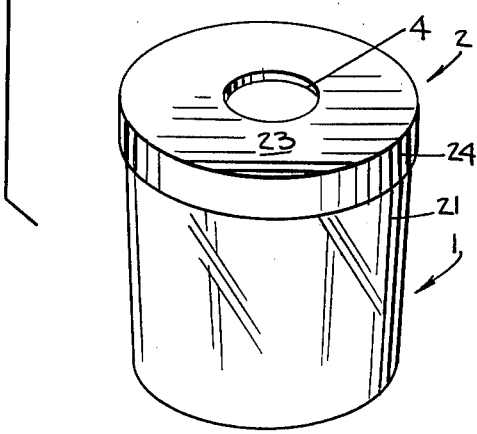
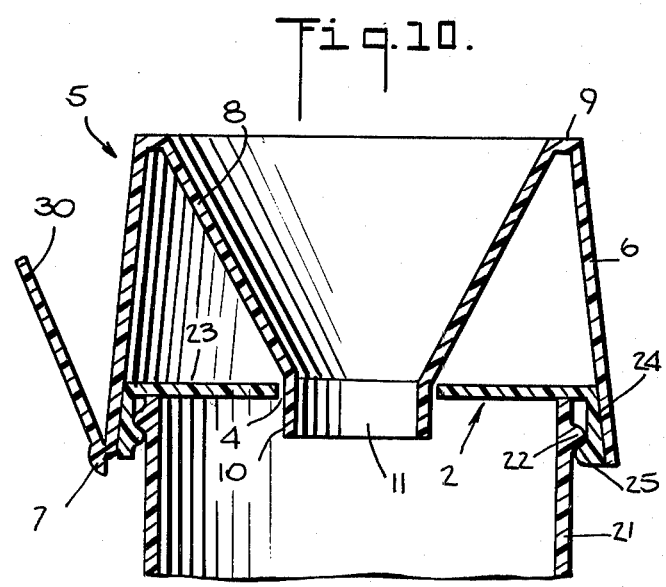

STERILE URINE COLLECTION DEVICE

DESCRIPTION

The present invention is directed to a improved mid-stream urine collection device and more particularly to a urine collection device which will keep the urine specimen uncontaminated until it is tested even when used by an untrained patient.

In the bacteriologic analysis of a urine specimen, the specimen is usually taken by the patient, without the assistance of trained personnel. It is imperative that the specimen be taken in such a manner that no extraneous contamination is introduced into the specimen or the container before, during, or after the sampling.

Sterile mid-stream urine collection devices currently available require complicated instructions and careful handling by the patient to avoid contamination. Additionally, these devices require the patient to handle the completely open specimen container after it is filled and then cover the container with screw-on or snap-on closure cap or lid.

Handling of the filled specimen container and lid in this manner presents the probability of spilling some of the urine, patient contamination of the outer and inner lip of the container by touching, and the introduction of airborne contamination into the specimen or the lid. Also, contamination of the lid by the patient in handling it or applying it to the container is possible. In addition, certain devices, such as plastic bags and thin plastic shells, intended to prevent contamination by the patient, are difficult to use and confuse the patient.

The present invention eliminates these drawbacks and has for an object the provision of improved urine collection devices which provides the taking of an uncontaminated mid-stream urine specimen by the patient.

Another object of the present invention is the provision of an improved urine collection device wherein the means for directing the fluid into the container is kept sterile until use.

Another object of the present invention is the provision of an improved urine collection device wherein the lid is kept sterile until use.

Another object of the present invention is the provision of an improved urine collection device wherein the device is provided with suitable identification so that there is virtually no chance of samples being mislabeled.

Another object of the present invention is the provision of an improved urine collection device whereby the inner portions of the container are protected from contamination until the article is used.

Other and further objects of the invention will be obvious upon an understanding of the illustrative embodiment about to be described, or will be indicated in the appended claims, and various advantages not referred to herein will occur to one skilled in the art upon employment of the invention in practice.

A preferred embodiment of the invention has been chosen for purposes of illustration and description and is shown in the accompanying drawings forming a part of the specification, wherein:

FIG. 1 is perspective view of a urine collection device made in accordance with the present invention.

FIG. 2 is an exploded view thereof.

FIG. 3 is a sectional view taken along line 3—3 of FIG. 1.

FIG. 8 is a perspective view of another embodiment of the present invention.

FIG. 9 is a sectional view taken along line 9—9 of FIG. 8.

FIG. 10 is a fragmentary sectional view showing the manner of removing the funnel assembly.

FIG. 11 is an exploded view showing the funnel assembly being removed.

Figure 4:
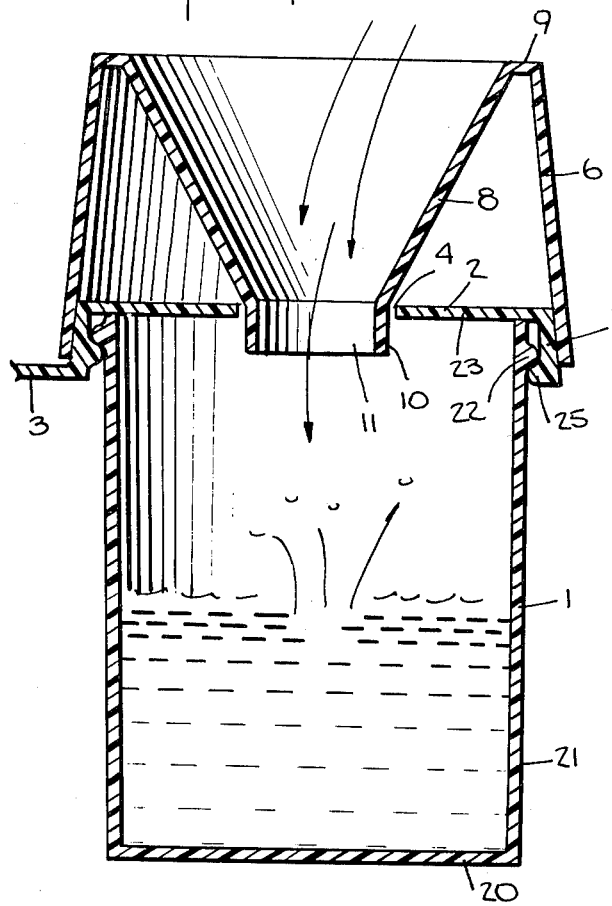
FIG. 4 is a sectional view similar to FIG. 3 showing the collection device during its use.

Relating to the drawings, the present invention comprises a specimen container 1 made of a clear translucent or opaque plastic or glass having a bottom 20 and side walls 21. A plastic or metal screw-on or snap-on closure cap or lid 2 having a cover portion 23 and depending skirt 24 is positioned over the finish 22 of container 1 and held in place by locking assembly 25 on skirt 24 cooperating with finish 22. A holding tab 3 extends from skirt 24 of cap 2 and is preferably integral therewith and a hole 4 is provided in the center of the cover portion.

A funnel assembly 5 consisting of a protective skirt 6, interior funnel 8, upper lip 9, lower central extension 10, and bottom hole 11 in extension 10 sits over cap 2 with the bottom extension 10 inserted within the opening 4 in the cover portion 23 of lid 2. The skirt portion 6 of the funnel assembly 5 is pressed fitted over skirt 24 of lid 2. A thin funnel cover 12, preferably made of paper or plastic with an outer skirt 17, and a preferably recessed center section 13 is provided and press fitted over funnel assembly 5. A die cut, pressure sensitive, waterproof label 14 with pull tab 15 extending there from and release paper 16 there below is placed in the center section 13 of the funnel cover 12. The label 14 has spaces for data to be written thereon.

As shown in the drawings in FIG. 1, when assembled, the device will have all interior surfaces sterile with no danger of contamination.

When the device is to be used, the patient's name and other pertinent data will be written in the spaces provided on the label 14 which has been glued to the top outer surface 13 of the funnel cover 12. The patient first lifts off the funnel cover 12 from the funnel and places it on a surface, either side up. Holding the tab 3, the patient voids into the exposed interior of container 1 through funnel 8 and opening 11 until the proper sample is taken (FIG. 4).

Figure 5:
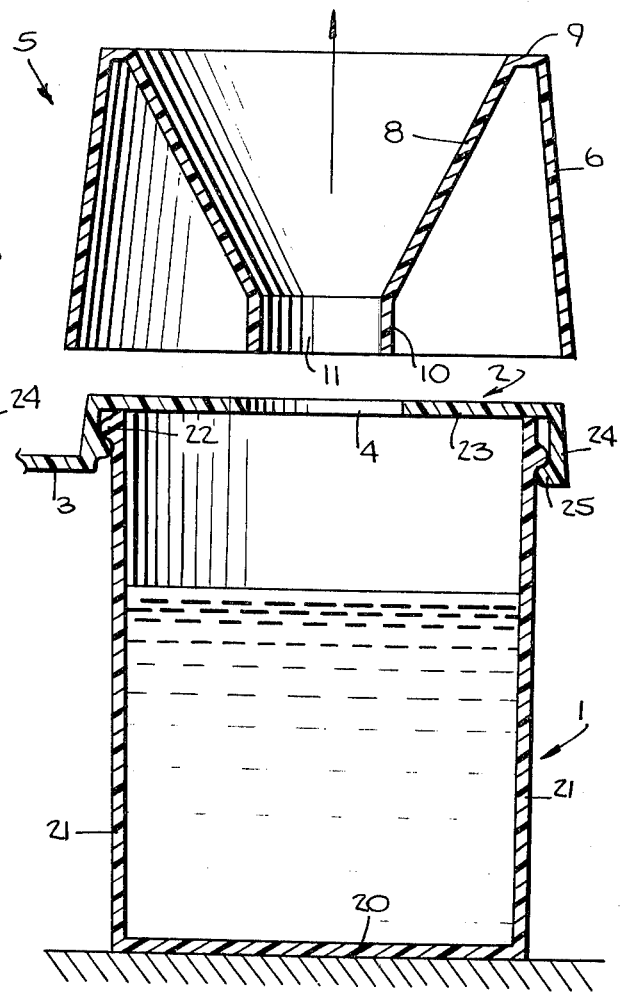
FIG. 5 is a sectional view similar to FIG. 4 showing the removal of the funnel assembly from the container.
Figure 6:
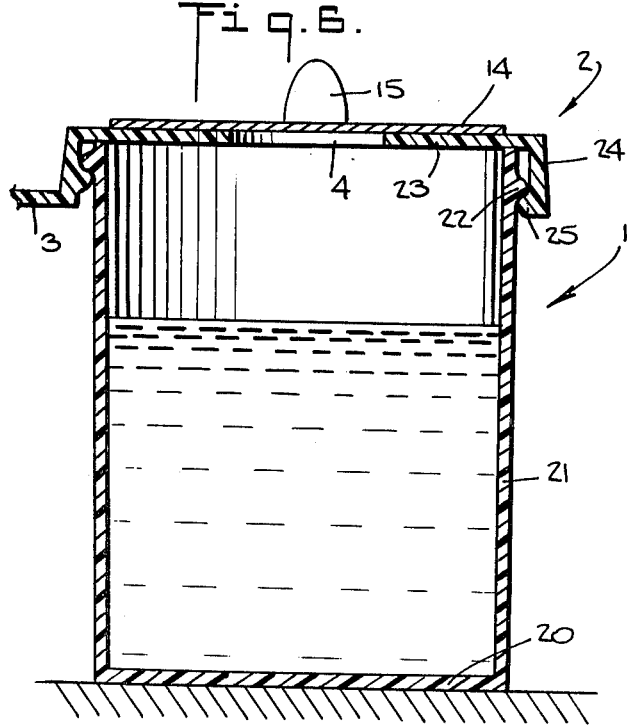
FIG. 6 is a sectional view similar to FIG. 5 showing the lid in its sealed position.
Figure 7:
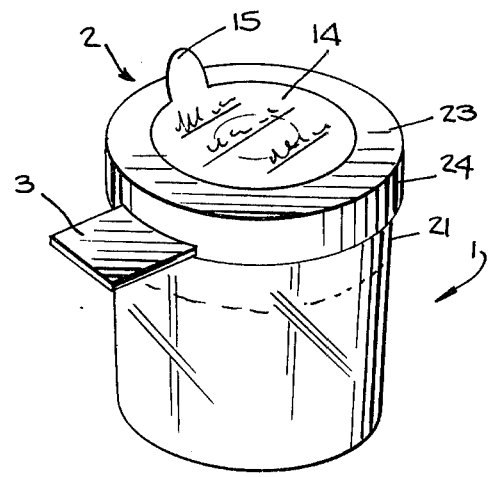
FIG. 7 is a perspective view showing the collection device after the lid has been applied.

The device is then placed on a level surface and the funnel assembly 5 is lifted off and discarded (FIG. 5). This exposes the hole 4 in the closure cap 2. By lifting the tab 15 the pressure sensitive label 14 is peeled from the funnel cover 12 leaving the release paper 16 glued to the cover. The label 14 is then applied over the hole 4 and the funnel cover 12 is discarded. The sealed sample is now ready for transport to a laboratory (FIGS. 6 and 7).

In a second embodiment of the device shown in FIGS. 8 to 11, wherein like reference numbers refer to the same structures as FIGS. 1 to 7, the holding tab 30 is integral with the lower skirt 6 of funnel assembly 5, instead of being a part of the lid 2, as in the embodiment shown in FIGS. 1 to 3.

Spaced lugs 7 are provided at the base of the protective skirt 6 to lock the funnel assembly 5 to the bottom of the skirt 24 on the lid 2. One of the spaced lugs 7 is at the inner end of tab 30. To remove the funnel assembly (FIG. 10) the patient flexes the holding tab 30 upwardly to release its associated lug 7 which has been formed on the under surface of the holding tab 30.

It will be seen that the present construction provides a mid-stream urine collection device in which the lid is not removed or applied at the time of use so that the inner and outer edges of the specimen container are not exposed to airborne or patient contamination. Also, the patient is not required to thread or snap a closure onto the container. Since the urine sample is directed through a small hole in the center of the lid by the funnel and the funnel extension protects the edges of the small hole in the lid from the urine, there is no contamination. By fitting tightly against the wall of the lid, the protective skirt 6 prevents airborne and patient contamination of the outer surfaces of the lid during use.

The funnel assembly may be removed without unthreading from the container and the funnel cover 12, funnel assembly 5, and screw-on or snap-on lid 2 maintain sterility of all interior surfaces of the device. The holding tab 3 (30) discourages touching of the interior of the funnel by the patient and the adhesive side of the label is maintained in a sterile condition until removed for application to the lid.

The label is additionally protected from contamination of the adhesive side by recessing the center area of the funnel cover. The funnel cover may be laid down in any position and the use of a water-proof pressure sensitive label 14 to seal the container with the use of a pressure sensitive label significantly larger than the hole prevents patient contact with the edge of the hole. The use of a pull tab on the label prevents patient contamination of the adhesive surface during removal from the release paper and during application to the lid. Gluing of the release paper 16 to the funnel cover prevents contamination of the adhesive surface during removal of the label.

In the second embodiment flexing of the holding tab 3 to release the lug 7 for removal of the funnel assembly accomplishes the same purpose.

It will thus be seen that the present invention provides an improved urine collection device wherein the means for directing the fluid onto the container as well as the lid is kept sterile until use; wherein the device is provided with suitable identification so that there is virtually no chance of samples being mislabeled; and wherein the inner portions of the container are protected from contamination until the article is used.

As many and varied modifications of the subject matter of this invention will become apparent to those skilled in the art from the detailed description given hereinabove, it will be understood that the present invention is limited only as provided in the claims appended hereto.

What is claimed is:

1. A urine collection device comprising a container, a lid closing said container, a funnel assembly mounted over said lid, said lid having an opening therein, said funnel assembly having a funnel member extending through the opening in the lid, a funnel cover mounted over the funnel assembly, a seal removably mounted on the device, said seal being adapted to be removed from the device and to be affixed to the lid to close the opening in the lid after the container is used and the funnel removed.

2. A collector as claimed in claim 1, wherein said lid is removably mounted on the open mouth of the container.

3. A collector as claimed in claim 2, wherein the funnel assembly has a skirt which is fitted over the lid.

4. A collector as claimed in claim 3, wherein said funnel assembly has an interior funnel.

5. A collector as claimed in claim 4, wherein the funnel has a lower extension extending through the opening in the lid.

6. A collector as claimed in claim 5, wherein said funnel cover has a skirt which is press-fitted over the skirt of the funnel assembly.

7. A collector as claimed in claim 6, wherein said funnel cover overlies the funnel assembly.

8. A collector as claimed in claim 7, wherein the funnel cover has a top surface extending across the interior funnel of the funnel assembly to close the said funnel.

9. A collector as claimed in claim 8, wherein said top surface of the funnel cover is depressed.

10. A collector as claimed in claim 9, wherein said seal is removably mounted on said depressed top surface.

11. A collector as claimed in claim 10, wherein said seal has means to adhere to the lid to close the opening therein.

12. A collector as claimed in claim 11, wherein said seal has a tab extending therefrom.

13. A collector as claimed in claim 12, wherein a release paper is interposed between the seal and the top surface of the funnel cover.

14. A collector as claimed in claim 13, wherein means are provided on the seal to permit data to be written thereon.

15. A collector as claimed in claim 14, wherein a holding tab extends from the container.

16. A collector as claimed in claim 15, wherein said holding tab extends from the skirt of the lid.

17. A collector as claimed in claim 15, wherein said holding tab extends from the skirt of the funnel assembly.

18. A collector as claimed in claim 17, wherein means are provided for operatively connecting said funnel and said lid together to hold the funnel on the lid.

19. A collector as claim in claim 18, wherein said means comprise at least one lug.

20. A collector as claimed in claim 19, wherein said means comprise a plurality of spaced lugs.

21. A collector as claimed in claim 20, wherein at least one of said lugs is integral and movable by the holding tab to release said funnel from said lid.

* * * * *